United States Patent [19]

Chonde et al.

[11] Patent Number: 4,897,352

[45] Date of Patent: Jan. 30, 1990

[54] ACRYLATE BASED ADSORBENT RESIN FOR THE IMMOBILIZATION OF ENZYMES

[75] Inventors: Yohannes Chonde, Midland, Mich.; Marsha A. Paul, Natick, Mass.

[73] Assignee: The Dow Chemical Company, Midland, Mich.

[21] Appl. No.: 144,205

[22] Filed: Jan. 15, 1988

[51] Int. Cl.[4] ...................... C12N 11/08; C12N 11/02; C12N 11/04; C12N 9/20

[52] U.S. Cl. .................................... 435/180; 435/177; 435/182; 435/198; 435/219

[58] Field of Search ............... 435/174, 177, 180, 182, 435/198, 219

[56] References Cited

U.S. PATENT DOCUMENTS

| | | | |
|---|---|---|---|
| 3,767,790 | 10/1973 | Guttag | 435/182 |
| 4,154,917 | 5/1979 | Miyake et al. | 528/113 |
| 4,224,198 | 9/1980 | Rembaum et al. | 260/8 |
| 4,537,911 | 8/1985 | Chonde | 521/28 |
| 4,614,751 | 9/1986 | Chonde | 521/31 |
| 4,798,793 | 1/1989 | Eigtved | 435/180 X |

Primary Examiner—David M. Naff

[57] ABSTRACT

Enzymes are immobilized on macroporous hydrophilic polymer beads by adsorption. The polymer beads are cross-linked, acrylate-based resins containing pendant hydroxy groups. The resins contain 10–70% methyl methacrylate, 10–70% methylacrylate, 5-14 40% ethylenically unsaturated monomer having at least one pendant hydroxyl group and 10–25% divinylbenzene. The resins provide immobilized enzyme preparations exhibiting excellent physical strength and stability as well as high enzyme activity.

20 Claims, No Drawings

ACRYLATE BASED ADSORBENT RESIN FOR THE IMMOBILIZATION OF ENZYMES

FIELD OF INVENTION

This invention relates to suspension polymerized macroporous hydrophilic polymer beads used as a support for immobilization of enzymes.

BACKGROUND OF THE INVENTION

Enzymes are useful as catalysts in various chemical reactions, and are preferably used in a purified form, separated from the organism that produced them. In such a purified form the enzyme is relatively unstable and easily denatured. It is also recovered with difficulty from an aqueous reaction medium. To overcome these difficulties, it is desirable to immobilize the enzyme on some insoluble carrier, where it may readily contact the reactants in said reaction medium, but where it benefits both from an increased stability and from easy recovery by simple processes such as filtration.

Ideally, the enzyme support material should possess the following characteristics:

(a) the enzyme immobilization upon the support should be accomplished with ease;
(b) the support should demonstrate chemical and physical stability, for example, to the effects of pH, salt, solvent, and mechanical compression;
(c) the support should be convenient to handle;
(d) the support should accommodate an acceptable loading of enzyme;
(e) the support should tolerate reasonable pressure drop associated with particle size, particle shape and flow rate;
(f) the support should stabilize the enzyme with respect to temperature, pH, salt, solvent and contaminants that might affect denaturation; and
(g) the materials should be stable to storage.

Enzymes can generally be immobilized on a solid support by three different methods: adsorption, covalent attachment or entrapment. Each method possesses its own advantages and disadvantages, but regardless of the method of attachment all immobilized enzyme systems are susceptible to incomplete binding of the enzyme during immobilization, a reduction in enzyme activity compared to the soluble enzyme and mechanical attrition under conditions of mechanical shear or compressive column pressure.

One of the most widely used commercial resins for the adsorptive immobilization of enzymes possesses a backbone composition of methyl methacrylate crosslinked with trimethylol propane trimethacrylate. Although this resin is capable of sufficient enzyme loadings, it has poor mechanical stability during process applications. For example, the resin easily breaks up under mechanical shear or compressive column pressure, resulting in plugging of the system and reduced expression of catalytic activity.

The object of this invention is the provide new, stable immobilized enzyme preparations which have excellent physical strength and enzyme loading capacity as well as high enzyme activity.

SUMMARY OF THE INVENTION

This invention relates to immobilized enzymes, more specifically to insoluble enzyme preparations in which the enzyme is adsorbed on an acrylate-based macroporous hydrophilic polymer bead.

The invention further relates to the methods of preparing such substances and to the methods of using such substances in enzyme-catalyzed processes.

DETAILED DESCRIPTION OF THE INVENTION

The present invention relates to macroporous, hydrophilic, spherical polyacrylate resin beads used as a support for the immobilization of enzymes. The resin beads of the present invention have a particle size range of from about 50 to about 2000 microns and an average pore diameter greater than about 200 Angstroms. The spherical polymer beads can be prepared by typical suspension polymerization techniques. The chemical composition of the starting polymer consists of the following monomeric components on the basis of weight percent of the total monomer mixture:

10–70 percent methyl methacrylate
10–70 percent methylacrylate
5–40 percent an ethylenically unsaturated monomer having at least one pendant hydroxyl group
10–25 percent divinylbenzene The preferred ethylenically unsaturated monomers having at least one pendant hydroxyl group include hydroxyalkylacrylates, hydroxyalkyl methacrylates and hydroxyalkyl allyl ethers.

Among the preferred polymer compositions are the following:

| | | |
|---|---|---|
| A | Methyl methacrylate | 30–60 percent by wt. |
| | Methylacrylate | 10–50 percent by wt. |
| | Hydroxy propylacrylate | 10–30 percent by wt. |
| | Divinylbenzene | 10–20 percent by wt. |
| B | Methyl methacrylate | 30–60 percent by wt. |
| | Methylacrylate | 10–50 percent by wt. |
| | Glyceryl allylether | 5–30 percent by wt. |
| | Divinylbenzene | 10–20 percent by wt. |
| C | Methyl methacrylate | 30–60 percent by wt. |
| | Methylacrylate | 10–50 percent by wt. |
| | Polyethylene Glycol methacrylate | 5–20 percent by wt. |
| | Divinylbenzene | 10–20 percent by wt. |

The divinylbenzene, which is employed as a crosslinking agent, can typically be of 55–80 percent purity.

The macroporous, hydrophilic, polyacrylate resins are effective supports for binding proteolytic enzymes (proteases and esterases) and lipolytic enzymes (lipases). These particular resins are most effective for the immobilization of lipases such as Candida lipase and Rhizopus lipase.

The immobilization of enzymes onto the resin beads can be generally carried out by contacting the enzyme and the beads at ambient temperature. Typically, about a 4 to 1 ratio of dry resin to crude enzyme can be shaken or stirred in a buffered aqueous solution with a pH of from about 4 to about 9. After adsorption of the enzyme is complete, the excess aqueous solution of enzyme can be decanted. The remaining polymer/enzyme complex can be rinsed with deionized water until the level of desorbing enzyme is undetectable.

The immobilized enzymes of the present invention can find use in food, pharmaceutical and agricultural applications. For example, the immobilized enzymes can be used in the resolution of optical isomers. In such a process a two (2) phase mixture of organic and aqueous solutions containing a racemic ester is contacted with the immobilized enzyme. The enzyme can specifically hydrolyze one enantiomer to the acid functionality that dissolves in the aqueous phase. The organic phase contains the unaffected ester of the other enantiomer. Such processes can be conducted in either a batch or continuous fashion. In the latter mode, the immobilized enzyme is preferably packed in a column through which the reactants are continuously circulated.

The following examples are given by way of illustration and are not to be construed as limitations of the invention. Many variations of the invention are possible without departing from the scope thereof.

EXAMPLE 1

Preparation of Polymer Beads

The macroporous hydrophilic spherical polymer beads were prepared by typical suspension polymerization techniques in a 3-liter stainless steel reactor. Prior to the polymerization reaction, all reaction mixtures and vessels were purged with nitrogen gas.

Into the purged 3-liter reactor, an aqueous solution containing 1248 grams (g) of deionized water, 250 g of 1 percent by weight carboxymethyl methylcellulose, and 1.5 g of sodium dichromate was charged. To this aqueous charge an organic mixture containing 450 g of methyl methacrylate, 300 g of hydroxypropyl acrylate, 156 g of methyl acrylate, 200 g of 55 percent purity divinylbenzene, 1.5 g of 50 percent tertiary-butyl peroctoate, 1 g of tertiary-butyl perbenzoate and 311 g of iso-octane was added. The mixture was polymerized under a nitrogen atmosphere under agitated conditions at 80° C. for eight (8) hours and at 110° C. for three (3) hours. At the end of the polymerization, the polymer beads were separated and washed with water. The iso-octane was removed by steam distillation. The dried opaque beads were characterized as follows:

| Appearance | opaque white |
|---|---|
| Porosity (cc of Hg/g bead) | 0.4 |
| Internal Surface area (m²/g bead) | 49 |
| Average pore diameter (Angstrom) | 730 |

EXAMPLE 2

Into a 3-liter reactor (purged as in Example 1), an aqueous solution containing 1248 g of deionized water, 250 g of 1 percent by weight of carboxymethyl methylcellulose and 1.5 g of sodium dichromate was charged. To this aqueous charge, an organic mixture containing 492 g of methyl methacrylate, 200 g of glyceryl allylether, 160 g of methyl acrylate, 200 grams of 55 percent purity divinylbenzene, 1.5 g of 50 percent purity tertiary-butyl peroctocte, 1 g of tertiary-butyl perbenzoate and 311 g of iso-octane was added. The mixture was polymerized under a nitrogen atmosphere under agitated conditions at 80° C. for eight (8) hours and at 110° C. for three (3) hours. At the end of the polymerization, the polymer beads were separated and washed with water. The iso-octane was removed by steam distillation. The dried opaque beads were characterized as follows:

| Average pore diameter (Angstroms) | 360 |
|---|---|
| Porosity (cc of Hg/g bead) | 0.48 |
| Internal surface area (m²/g bead) | 116 |

EXAMPLE 3

Immobilization of an Esterase

Carboxyl liver esterase (E.C. 3.1.1.1, Sigma Chemical Co., 144.5 mg) was dissolved in 20 ml of 0.01M borate buffer. A 100 microliter aliquot was added to 25 ml of solution containing 0.167 ml of ethyl butyrate. The reaction was stirred while the pH was maintained at a value of 8.0 using a pH stat. The enzymatic hydrolysis rate was calculated to be $1.3 \times 10^{-6}$ equiv/min/mg enzyme.

To the remaining 20 ml of enzyme, 2.0 g of the resin of Example 1 was added and the mixture was stirred for 30 minutes. The resin was collected by suction filtration and was assayed for enzyme activity as above except 1 g of resin was used in place of 100 microliters of dissolved enzyme. The observed resin enzyme activity was $4 \times 10^{-4}$ equiv/min/g resin.

EXAMPLE 4

Immobilization of a Lipase

Lipase enzyme was immobilized in a similar manner as Example 3 on the resin of Example 1. Candida Lipase (E.C. 3.1.1.3, Sigma Chemical Co., Lipase type VII) was dissolved to make a solution of 56 mg in 28 ml of 0.01M borate buffer. A 3.0 ml aliquot was taken and was added to 25 ml of 0.01M borate buffer pH 8.0 containing 0.5 ml of ethyl butyrate. The stirred reaction was held at a pH of 8.0 using a pH stat. An activity of $1.3 \times 10^{-7}$ equiv/min/mg enzyme was obtained.

To the remainder of the enzyme solution, 2.0 g of the resin was added and stirred for 30 minutes. The resin was filtered out and 1.0 g was added to a second pH stat assay solution. The observed activity was $6.3 \times 10^{-7}$ equiv/min/g resin.

EXAMPLE 5

Immobilization of a Protease

Similarly the resin of Example 1 was used to immobilize subtilisin enzyme (Sigma Chemical Co., protease type VIII). The enzyme was dissolved (20 mg) in 10 ml of 0.05M tris/0.2M $CaCl_2$ buffer. A 50 microliter aliquot was added to 25 ml of buffer containing 0.112 g of N-Acetyl phenylalanine ethyl ester. The reaction was maintained at pH 7.5 with a pH stat resulting in an enzyme activity of $5.6 \times 10^{-5}$ equiv/min/mg enzyme.

To the remainder of the enzyme solution, 2.0 g of resin was added and the mixture was stirred for 30 minutes. The resin was collected and assayed using 0.1 g in the above assay procedure. An activity of $2.6 \times 10^{-5}$ equiv/min/g resin was observed.

EXAMPLE 6

A variety of enzymes were adsorbed onto the resin beads of Examples 1 and 2 by the same procedures outlined in Examples 3-5. Activities were measured by ethyl butyrate hydrolysis in aqueous buffer. The results are summarized in Table I.

TABLE 1

| ENZYME BINDING TO VARIOUS POLYMER BEAD SUPPORTS | | | | |
|---|---|---|---|---|
| | FAP[1] | MAP[2] | CANDIDA[3] | LPL[4] |
| Resin Example 2 | | | | |
| Percent Bound | 0 | 51 | 79 | 100 |

TABLE 1-continued

| ENZYME BINDING TO VARIOUS POLYMER BEAD SUPPORTS | | | | |
|---|---|---|---|---|
| | FAP[1] | MAP[2] | CANDIDA[3] | LPL[4] |
| Percent Expressed | 9 | 80 | 45 | 30 |
| Resin Example 1 | | | | |
| Percent Bound | 13 | 87 | 48 | 100 |
| Percent Expressed | 1055 | 81 | 80 | 28 |

[1]Amano F-AP (Rhizopus lipase)
[2]Amano M-AP (Mucor miehei)
[3]Candida cylindracea lipase (Sigma)
[4]Lipoprotein lipase (Sigma, from pseudomonas)

What we claim is:

1. A process for preparing an immobilized enzyme which comprises adsorbing an enzyme on macroporous, hydrophilic resin beads comprised of:
   10–70 weight percent methyl methacrylate;
   10–70 weight percent methylacrylate;
   5–40 weight percent ethylenically unsaturated monomer having at least one pendant hydroxyl group; and
   10–25 weight percent divinylbenzene.

2. The process of claim 1 wherein the enzyme is an esterase, a protease or a lipase.

3. The process of claim 2 wherein the enzyme is a lipase.

4. The process of claim 3 wherein the lipase is derived from Candida or Rhizopus organisms.

5. The process of claim 1 wherein the ethylenically unsaturated monomer having at least one pendant hydroxyl group is selected from the group consisting of hydroxyalkylacrylate, hydroxyalkyl methacrylates and hydroxyalkyl allyl ethers.

6. A process for preparing an immobilized enzyme which comrises adsorbing an enzyme on macroporous, hydrophilic resin beads comprised of:
   30–60 weight percent methyl methacrylate;
   10–50 weight percent methylacrylate;
   5–30 weight percent ethylenically unsaturated monomer having at least one pendant hydroxyl group; and
   10–20 weight percent divinylbenzene.

7. The process of claim 6 wherein the enzyme is an esterase, a protease or a lipase.

8. The process of claim 7 wherein the enzyme is a lipase.

9. The process of claim 8 wherein the lipase is derived from Candida or Rhizopus organisms.

10. The process of claim 6 wherein the ethylenically unsaturated monomer having at least one pendant hydroxyl group is selected from the group consisting of hydroxyalkylacrylates, hydroxyalkyl methacrylates and hydroxyalkyl allyl ethers.

11. An immobilized enzyme according to claim 1.
12. An immobilized enzyme according to claim 2.
13. An immobilized enzyme according to claim 3.
14. An immobilized enzyme according to claim 4.
15. An immobilized enzyme according to claim 5.
16. An immobilized enzyme according to claim 6.
17. An immobilized enzyme according to claim 7.
18. An immobilized enzyme according to claim 8.
19. An immobilized enzyme according to claim 9.
20. An immobilized enzyme according to claim 10.

* * * * *